United States Patent
Bina et al.

(10) Patent No.: US 7,172,421 B2
(45) Date of Patent: Feb. 6, 2007

(54) ENDODONTIC ROOT-CANAL JIG AND FIXTURE

(76) Inventors: Shahin I. Bina, 928 11th St., #2, Santa Monica, CA (US) 90403; Danny H. Kuighadush, 139-50 Pershing Crest, Briarwood, NY (US) 11435

(*) Notice: Subject to any disclaimer, the term of this patent is extended or adjusted under 35 U.S.C. 154(b) by 297 days.

(21) Appl. No.: 10/771,835

(22) Filed: Feb. 3, 2004

(65) Prior Publication Data

US 2004/0219482 A1 Nov. 4, 2004

Related U.S. Application Data

(60) Provisional application No. 60/444,848, filed on Feb. 4, 2003.

(51) Int. Cl.
*A61C 3/02* (2006.01)
*B23B 51/00* (2006.01)

(52) U.S. Cl. ..................... 433/165; 408/202

(58) Field of Classification Search ............ 433/165, 433/126, 114, 141, 146, 147, 72, 75; 408/202
See application file for complete search history.

(56) References Cited

U.S. PATENT DOCUMENTS

| | | | | |
|---|---|---|---|---|
| 3,620,637 A | * | 11/1971 | Brown | 408/202 |
| 4,019,827 A | * | 4/1977 | Christianson et al. | 408/202 |
| 4,212,639 A | * | 7/1980 | Schaffner | 433/72 |
| 5,895,389 A | * | 4/1999 | Schenk et al. | 606/96 |
| 6,585,143 B1 | * | 7/2003 | Schultz | 227/147 |
| 6,905,486 B2 | * | 6/2005 | Gibbs | 604/264 |

* cited by examiner

*Primary Examiner*—Cris L. Rodriguez
*Assistant Examiner*—Candice C. Stokes
(74) *Attorney, Agent, or Firm*—Sofer & Haroun, LLP

(57) ABSTRACT

A device for use in an endodontic root canal, performed using a dental drill hand set has a first upper unit coupled to the drill hand set. The first upper unit is cylindrical in shape and has a first drill shank shaft therethrough. The upper unit has a first threading on its outside surface. A second bottom unit, cylindrical in shape, is also provided, having a second drill shank shaft therethrough. The second bottom unit has a second corresponding threading on its inside surface. When the second bottom unit is screwed onto the first upper unit a root canal jig is formed having a set height and allowing a shank from the drill hand set to pass through the first and second drill shank shafts, such that when the drill shank of the drill hand set is drilled into an affected tooth for a root canal, the drill shank is prevented from drilling along its entire length into the root of the affected tooth when the bottom of the root canal jig contacts the top of the tooth.

17 Claims, 9 Drawing Sheets

US 7,172,421 B2

ENDODONTIC ROOT-CANAL JIG AND FIXTURE

RELATED APPLICATION

This application is related to and claims the benefit of priority from U.S. Provisional Patent Application No. 60/444,848, filed on Feb. 4, 2003, the entirety of which is incorporated herein by reference.

FIELD OF THE INVENTION

This invention is related to root canal operations. More specifically, this invention is related to improved equipment for performing endodontic root canals.

BACKGROUND OF THE INVENTION

When performing root canals, it is essential to drill into the root of the tooth all the way down to the apex. It is essential that the drilling terminate nearly exactly at the apex, as over-drilling through the apex may result in permanent damage to the tooth, and under drilling, or stopping before the apex, may not remove all of the necessary material, resulting in an increased chance for future infection.

Presently, while performing root-canals a dentist first measures the dept of the root to the apex by inserting a needle into the tooth and performing an X-ray. The height of the needle inserted within the tooth is noted and then added to the distance between the end of the needle and the apex in the X-ray. This combined height of the needle within the tooth and the distance from the apex is added together to get the total height of the root.

After the height of the root is determined, a visual stopper, such as rubber colored stopper, is positioned on the shank of the drill set in order to provide the dentist with a visual marking on the shank as to the height of the root to be drilled. The dentist then begins drilling the shank down into the root of the tooth until the stopper is flush with the top of the tooth.

There are several drawback associated with this method for performing root canals. Most importantly, the stopper or marker disposed on the shank does not act as a physical stopper but rather a visual indicator only prompting the dentist to stop drilling on their own. However, a number of occurrences can result in the dentist over drilling the root. For example, problems that could arise include but are not limited to: the dentist's hand or eyes may be fatigued after performing many root canals; the rubber stopper may move during drilling; the mouth may be small resulting in improper or insufficient lighting; the tooth may be chipped providing an uneven stopping point; the hole within the tooth may be too large to properly gauge when the stopper has reached the top of the tooth; or the angle of the handset may impair the dentist's view.

In each of these instances it is possible that the dentist may over drill or under drill the root, overshooting or undershooting the apex, causing lasting damage to the affected tooth.

OBJECT AND SUMMARY OF THE INVENTION

It is the object of the present invention to overcome the drawbacks associated with the prior art devices used in root-canal.

Thus, it is one object of the present invention to provide a jig and fixture that will automatically stop the drilling process in a root canal at the intended depth so as to prevent over drilling or under drilling of the patients tooth root.

It is another object of the present invention, to provide a jig ring, stem and housing assembly that will automatically stop the drilling process in a root canal at the intended depth so as to prevent over drilling or under drilling of the patients tooth root.

To this end the present invention provides for a device for use in an endodontic root canal, performed using a dental drill hand set. The device comprises a root canal jig having a top and bottom and an adjustable height. The top of the root canal jig is attached to the dental drill hand set and configured to allow a drill shank to pass therethrough. The root canal jig is configured to allow a portion of the drill shank, less than the total height of the drill shank, to be exposed out from the bottom of the root canal jig, such that when the bottom of the root canal jig contacts the top of an affected tooth, the drill shank is prevented from drilling any further into the affected tooth.

BRIEF DESCRIPTION OF THE DRAWINGS

The various objects, advantages and novel features of the present invention will be more readily understood from the following detailed description when read in conjunction with the appended drawings, in which.

DETAILED DESCRIPTION OF THE PREFERRED EMBODIMENTS

Figure 1:
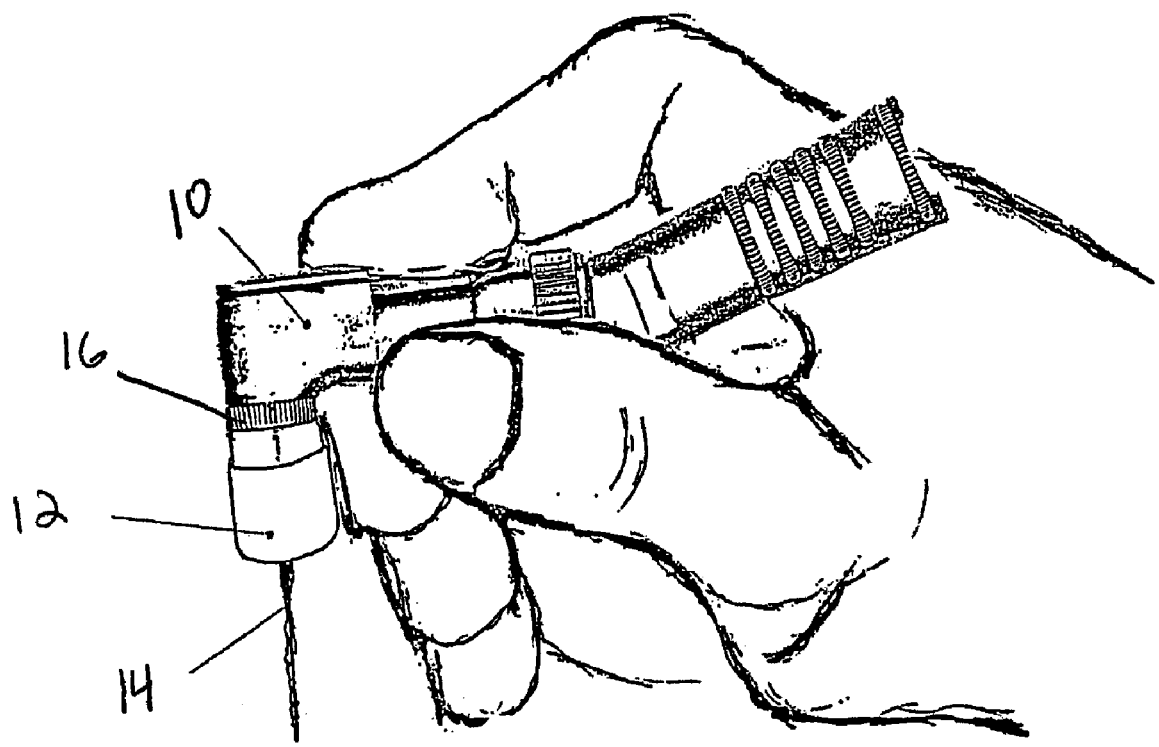
FIG. 1 is a side view of a drill hand set having the root canal jig attached thereto, in accordance with one embodiment of the present invention.

Reference is now made to FIG. 1 showing a drilling device or dental hand set 10 or having an attached root canal jig 12 and a standard drill shank 14. The drill shank is preferably a flexible nickel-titanium rotary file, however, any drill shank used for root canals can be used in conjunction with the present invention. Root canal jig 12 is shown attached to dental hand set 10 at an attachment region 16.

In one embodiment of the present invention, root canal jig 12 is attached to dental hand set 10 by removing a standard threaded ring and screwing jig 12 onto the exposed threaded region. However, this is in no way intended to limit the scope of the present invention. Root canal jig 12 can be attached in by any number of means to dental hand set 10. For example, a standardized docking adapter (not shown) may be provided so that a single root canal jig 12 can be fitted on to a variety of standard dental hand sets. For the purposes of illustration, root canal jig 12 will be discussed throughout as being attached directly onto the exposed threaded region of drill hand set 10.

Figure 2:
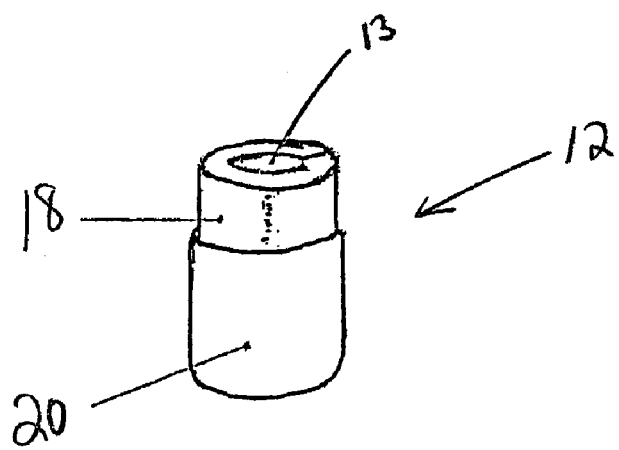
FIG. 2 is a side view of the root canal jig from FIG. 1, in accordance with one embodiment of the present invention.

Turning to FIG. 2, a close up is provided of root canal jig 12. A first top unit 18 and a second bottom unit 20, when combined form root canal jig 12 with drill shank shaft 13.

Top unit 18 is fashioned as a tubular cylindrical element constructed of any surgical grade metal or polymer, that is of sufficient rigidity to withstand the pressure of the dentist's hand when the root canal is being performed. Top unit 18 is threaded on the outer side and is smooth on the inner side. At the top of the inner side, top unit 18 may maintain a small threaded region for screwing onto dental hand set 10. Alternatively, the inner portion of top unit 18 may maintain a standardized docking adapter (not shown) mentioned above.

Bottom unit 20 of root canal jig 12 is also fashioned as a tubular cylindrical element constructed of any surgical grade metal or polymer, preferably the same as top unit 18. Bottom unit 20 is threaded on the inner side and is smooth on its outer side.

Figure 3:
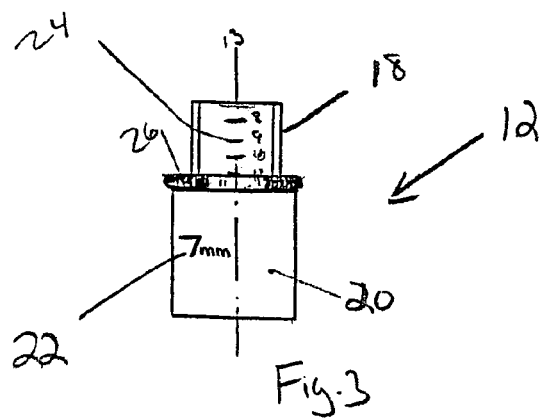
FIG. 3 is a side view of the root canal jig from FIG. 2 with height markings, in accordance with one embodiment of the present invention.

As illustrated in FIG. 3, a first primary marker 22 is disposed on the bottom unit 20 that corresponds to the height of bottom unit 20. In the example of FIG. 3 bottom unit 20 has a height of 7 mm. This is intended as only one example of standard height measurement for root canal jig 12, any similar markings or height measurements can be used.

Also, illustrated in FIG. 3, a series of adjustment markers 24 are located in descending order on top unit 18 of root canal jig 12. The numbers of adjustment markers 24 represent the total height of root canal jig 12 from the bottom of bottom unit 20 to the top of top unit 18. In the illustration on FIG. 3 the first number in adjustment markings 24 is 8, then 9, then 10 then 11. As the top unit 18 is screwed relative to bottom unit 20 the inner top unit 18 extends outward from the top of outer bottom unit 20, extending the overall height of root canal jig 12. At the current setting in FIG. 3, root canal jig 12 is set to a total height of 11 millimeters.

It is understood that the depth of the root is determined by use of X-ray and needle according to standard practice, as noted in the background portion. It is noted that any means for detecting the depth of the root to be drilled can be used in conjunction with this invention. Root depths for teeth commonly range in the area of 13–19 mm, however, other depths are of course possible based on the age and size of the patient.

It is also understood that the standard length of drill shank 14 is approximately 25 mm–32 mm in length, from the bottom of the drill hand set 10. It is noted that the length of drill shank 14 referred to throughout this application, is the effective length drill shank 14, or the amount that extends beyond the bottom of drill hand set 10. This of course is in no intended to limit the use of the present invention, root canal rig 12 can be manufactured in a wide range of heights to be used in conjunction with any length drill shank 14.

When attempting to determine the necessary total height of root canal jig 12, a simple formula is employed:

$$HS-HR=HJ$$

where HS=Height of Shank; HR=Height of Root; and HJ=Height of root canal Jig For example, if the dentist is using a 29 mm drill shank 14, and the height or depth of the root is 18 mm, then root canal jig must be set to 11 mm. By screwing top unit 18 relative to bottom unit 20 the total height of root canal jig 12 is set to 11 mm as indicated on adjustment markings 24 on top unit 18.

Figure 4:
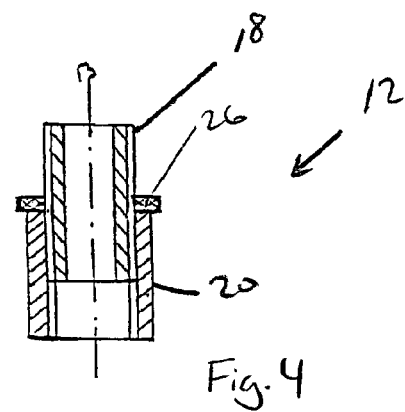
FIG. 4 is a cross-sectional side view of the root canal jig from FIG. 2, in accordance with one embodiment of the present invention.

As illustrated in FIGS. 3 and 4 once the desired height of root canal jig 12 is reached, a locking ring 26 is lowered down the outer threading of top unit 18 until it reaches the top of bottom unit 20. When locking ring 26 is touching top unit 20, the final height of root canal jig 12 is set.

Figure 5:
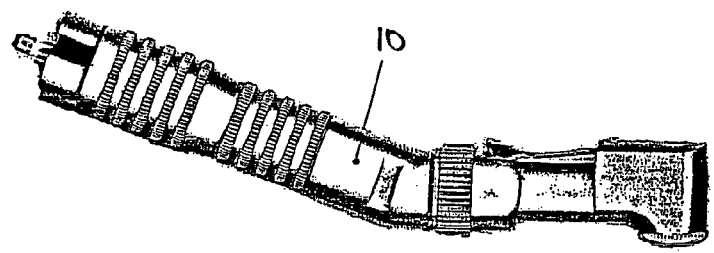
FIG. 5 is an exploded side view of the drill hand set, root canal jig and drill shank from FIG. 1 with a patient's tooth, in accordance with one embodiment of the present invention.
Figure 5:
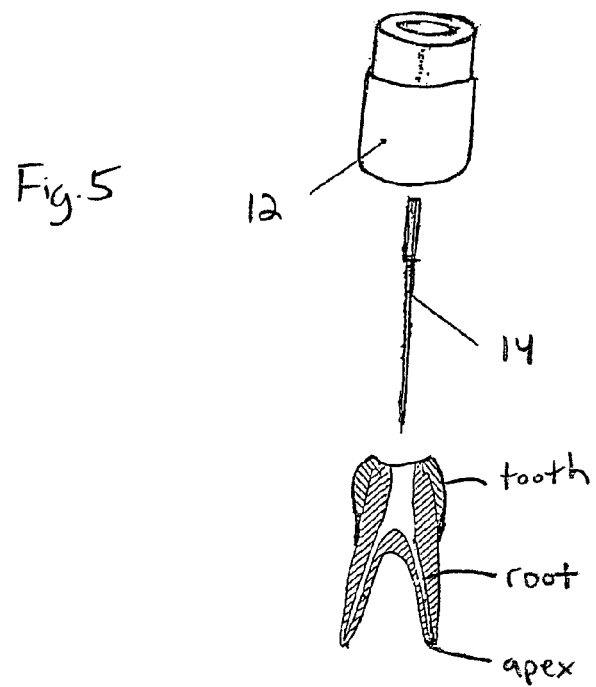
Figure 6:
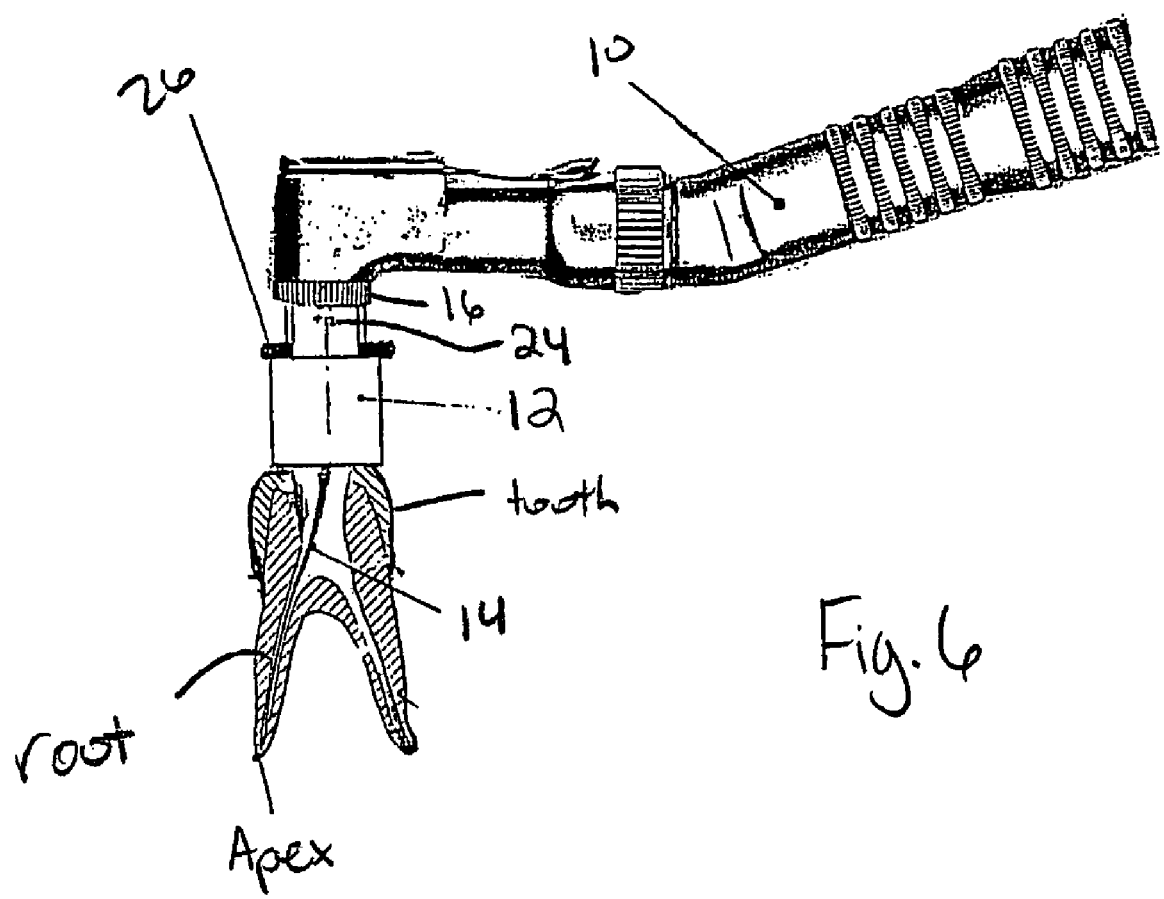
FIG. 6 is combined side view of the drill hand set, root canal jig, drill shank and patient's tooth from FIG. 5, in accordance with one embodiment of the present invention.

As illustrated in FIG. 5, once the height of root canal jig 12 is set, it is attached to the drill hand set 10 along with drill shank 14. As shown in FIG. 6, the drill hand set 10, with drill shank 14 extending though drill shank shaft 13, and root canal jig 12 in place, is lowered onto the tooth and the root is drilled with precision to the apex. Thus, as a result of attaching root canal jig 12 to drill hand set 10, the dentist, when performing the root canal surgery is limited to pressing drill shank 14 into the tooth when the bottom of jig 12 contacts the top of the affected tooth allowing only the exact correct depth of 18 mm to be drilled into the root, effectively preventing over or under drilling.

Figure 7A:
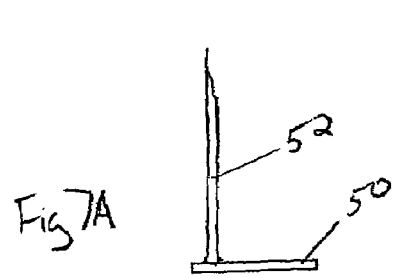
FIG. 7A is a side view of a jig ring, in accordance with another embodiment of the present invention.
Figure 7B:
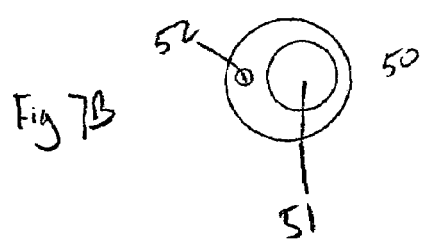
FIG. 7B is a top view of the jig ring from FIG. 7A, in accordance with one embodiment of the present invention.
Figure 8A:
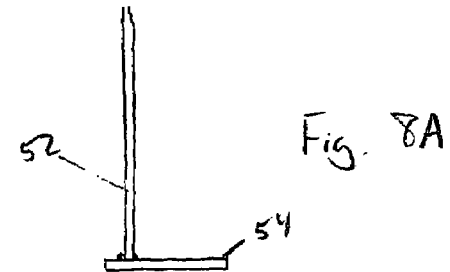
FIG. 8A is a side view of a jig horseshoe, in accordance with another embodiment of the present invention.
Figure 8B:
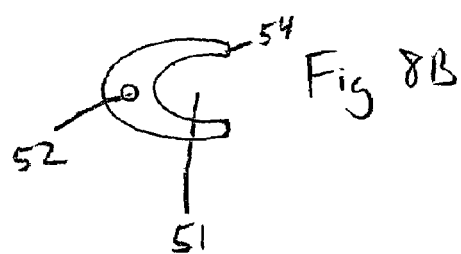
FIG. 8B is a top view of the jig horseshoe from FIG. 8A, in accordance with one embodiment of the present invention.

In another embodiment of the present invention, a first jig ring 50 and stem 52 are shown in FIGS. 7A and 7B. A second version, illustrated in FIGS. 8A and 8B, shows a horseshoe ring 54 with stem 52. Jig ring 50 and horseshoe ring 54 are preferably constructed of a surgical grade metal or polymer. Each of jig ring 50 and horseshow ring 54 are formed with a drill shaft opening 51, configured to allow drill shank 14 to pass through. For the purposes of illustration, jig ring 50 is used throughout to describe the correlating features of the present invention, however, it is understood that horseshow ring 54 is interchangeable throughout.

Stem 52, used with both jig ring 50 and horseshoe ring 54, is preferably constructed from the same nickel-titanium alloy that is used for drill shank 14. As such, stem 52 is constructed of a material that is sufficiently rigid to resist the dentist's hand pressure, but at the same time remains flexible enough to bend around a corner as described below.

Figure 9:
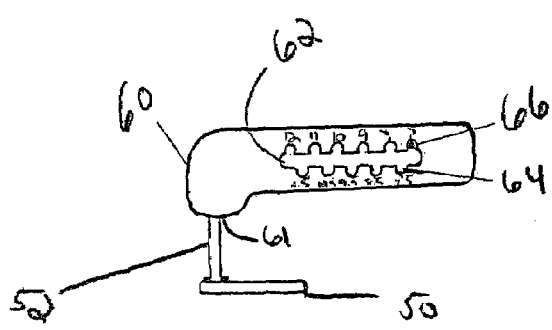
FIG. 9 is a side view of a jig ring, stem and notch stem housing, in accordance with one embodiment of the present invention.

As illustrated in FIG. 9, a notched stem housing 60 is provided which roughly mirrors the shape of the drilling end of drill hand set 10. Notched stem housing 60 is preferably constructed of the same material as drill handset 10, however, it can be constructed of any surgical grade metal or polymer that is able to support the attached stem 52. Notched stem housing 60 is configured to be attached to drill hand set 10 such that the end 61 of housing 60, where stem 52 emerges, is roughly co-equal in height with the point where drill shank 14 emerges from drill hand set 10.

Notched stem housing 60 is fitted with a notch opening 62 along the side that is exposed when it is attached to drill hand set 10. Notch opening 62 is outfitted with a number of individual dimple acceptors 64, each of which is numbered with a certain measurement.

For example, as illustrated in FIG. 9, first dimple acceptor 64 on the top is labeled as 7 mm. Second dimple acceptor 64 to the bottom is labeled at 7.5 mm. Dimple acceptors 64 are labeled consecutively as such, in 0.5 mm steps. It is understood of course that the measurements associated with each dimple acceptor 64 can be labeled in accordance with any such numbering system.

Regardless of the numbering systems used to label each dimple acceptor 64, each dimple acceptor 64 in notch opening 62 represents a different height that stem 52 will extend from the bottom of drill hand set 10, (bottom being defined by the point at which drill shank 14 emerges from drill hand set 10) until it reaches the bottom of the attached jig ring 50.

Figure 10:
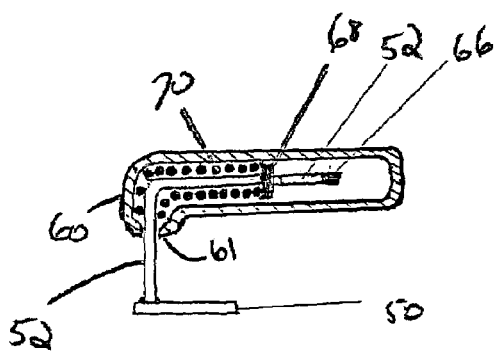
FIG. 10 is a cross-sectional side view of a jig ring, stem and notch stem housing from FIG. 9, in accordance with one embodiment of the present invention.
Figure 11:
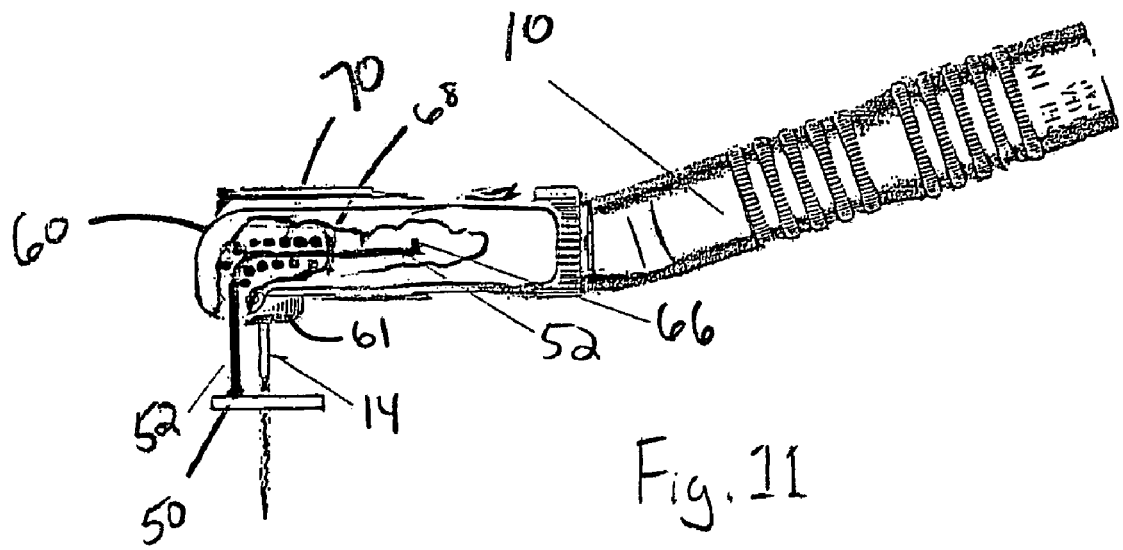
FIG. 11, is a side view of the notch stem housing from FIG. 9, attached to a drill hand set, in accordance with one embodiment of the present invention.
Figure 12:
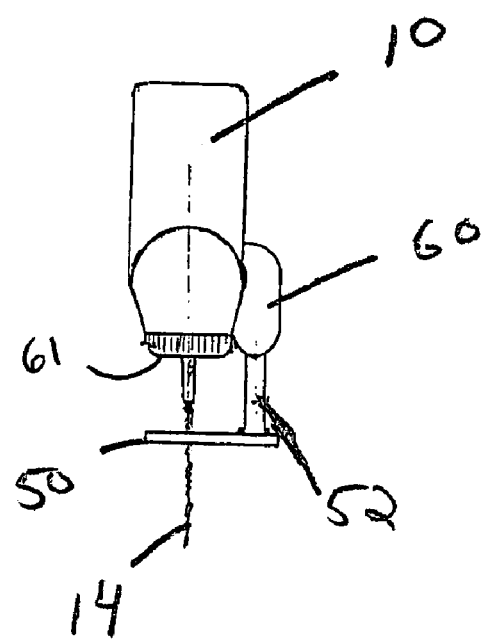
FIG. 12, is a front view of the notch stem housing from FIG. 9, attached to a drill hand set, in accordance with one embodiment of the present invention.

FIG. 10 illustrate the mechanism disposed in housing 60. As illustrated in FIG. 10, stem 52 is outfitted with a dimple 66 disposed within notched stem housing 60 and facing in the same direction as notch opening 62. A spring flange 68 is also disposed on stem 52, within notched stem housing 60, in a position between jig ring 50 and dimple 66. On the opposite side of flange 68 from dimple 66, a biasing spring 70 is positioned within notched stem housing 60 in such a way so as to act against flange 68 to bias stem 52 and its attached dimple 66 in a direction away from the drilling end of drill hand set 10 and towards the first dimple acceptor 64 with the lowest labeled measurement. FIGS. 11 and 12 illustrate various views of notched stem housing 60 disposed on drill hand set 10 in accordance with one embodiment of the present invention.

Thus, as illustrated in FIGS. 9 and 10, the height of bottom of jig ring 50 can be adjusted by the dentist by removing dimple 66 from dimple acceptor 64 and moving it to the appropriate dimple acceptor 64 for the desired height. If the dentist requires a lower height setting, they can remove dimple 66 from dimple acceptor 64 into the middle of notch opening 62 and allow biasing spring 70 to work against flange 68, moving stem 52 and the attached dimple 66 down to the lower height settings.

Using the same measurements equations as discussed in detail in the first embodiment, the necessary total height is calculated using a simple formula.

$$HS-HR=DS$$

where HS=Height of Shank; HR=Height of Root; and DS=Dimple Setting

For example, if the dentist is using a 28 mm drill shank 14, and the height or depth of the root is 18 mm, then dimple 66 is moved to the appropriate 10 mm dimple acceptor 64, such that the distance between the bottom of drill hand set 10 and the bottom of jig ring 50 is set to 10 mm, allowing only 18 mm of drill shank 14 to extend below the bottom of jig ring 50. As such, when drill shank 14 is drilled into the root of the affected tooth, drill hand set 10 will be stopped when the bottom of jig ring 50 contacts the top of the tooth, allowing for exactly 18 mm of drilling depth into the affected tooth root. It is understood that notch stem housing 60 and notch acceptors 64 can be manufactured in a wide range of heights in accordance with any desired requirements.

Figure 13:
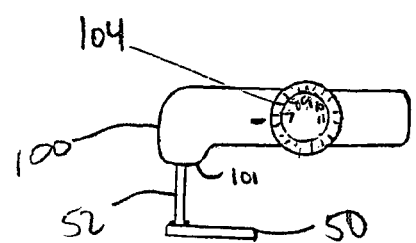
FIG. 13 is a side view of a jig ring, stem and dial stem housing, in accordance with another embodiment of the present invention.

In another embodiment of the present invention, according to FIG. 13, a dialed stem housing 100 is provided, which roughly mirrors the shape of the drill hand set 10 at the drilling end. Dialed stem housing 100 is preferably constructed of the same material as drill handset 10, however, it can be constructed of any surgical grade metal or polymer that is able to support the attached stem 52. Dialed stem housing 100 is configured to be attached to drill hand set 10, such that the end of housing 100, where stem 52 emerges, is roughly co-equal in height with the end 101 of housing 100 where drill shank 14 emerges from drill hand set 10.

Dialed stem housing 100 is fitted with a dial opening 102 along the side that is exposed when it is attached to drill hand set 10, as illustrated in FIG. 9. Dial opening 102 is configured to support a height dial 104, numbered with varying height measurements about the circumference. Height dial 104 is labeled consecutively with height measurement ranging in 0.5 mm steps. Typically, the height measurements range from 7 mm up to 12 mm, however, it is understood that the both the range, increments and denomination of the measurements on height dial 104 can be manufactured in accordance with any similar measurements.

Regardless of the numbering systems used to label height dial 104, each height marking on height dial 104 represents a different height that stem 52 will extend from the bottom of drill hand set 10, (bottom being defined by the point at which drill shank 14 emerges from drill hand set 10) until it reaches the bottom of the attached jig ring 50.

Figure 14:
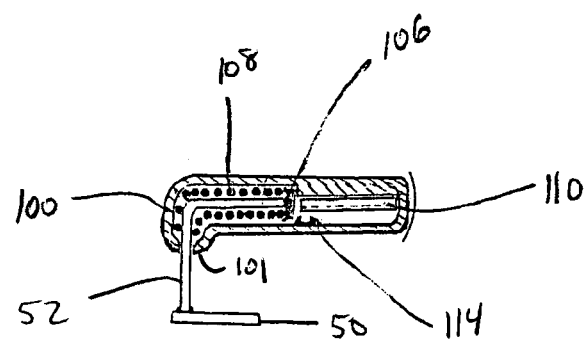
FIG. 14 is a cross-sectional side view of a jig ring, stem and dial stem housing from FIG. 13, in accordance with one embodiment of the present invention.

FIG. 14 illustrate the mechanism disposed in housing 100. As illustrated in FIG. 14, stem 52 is outfitted with a spring flange 106, disposed on stem 52, within dial stem housing 100. On jig ring 50 side of flange 106, a biasing spring 108 is positioned within dial stem housing 100 in such a way so as to act against flange 106 to bias stem 52 in a direction away from the drilling end of drill hand set 10 and towards the rear of dial stem housing 100.

Figure 15:
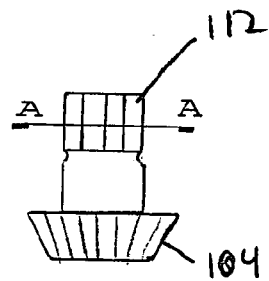
FIG. 15 is a top view of a toothed wheel and dial gauge from the dial stem housing in FIG. 13, in accordance with one embodiment of the present invention.
Figure 16:
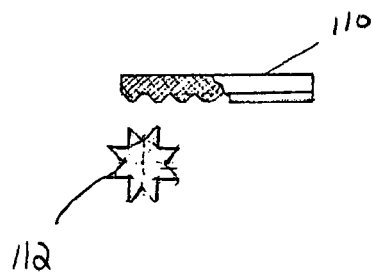
FIG. 16 is a cross section of the toothed wheel from FIG. 15 along the A—A axis and a corresponding toothed bar, in accordance with one embodiment of the present invention.
Figure 17:
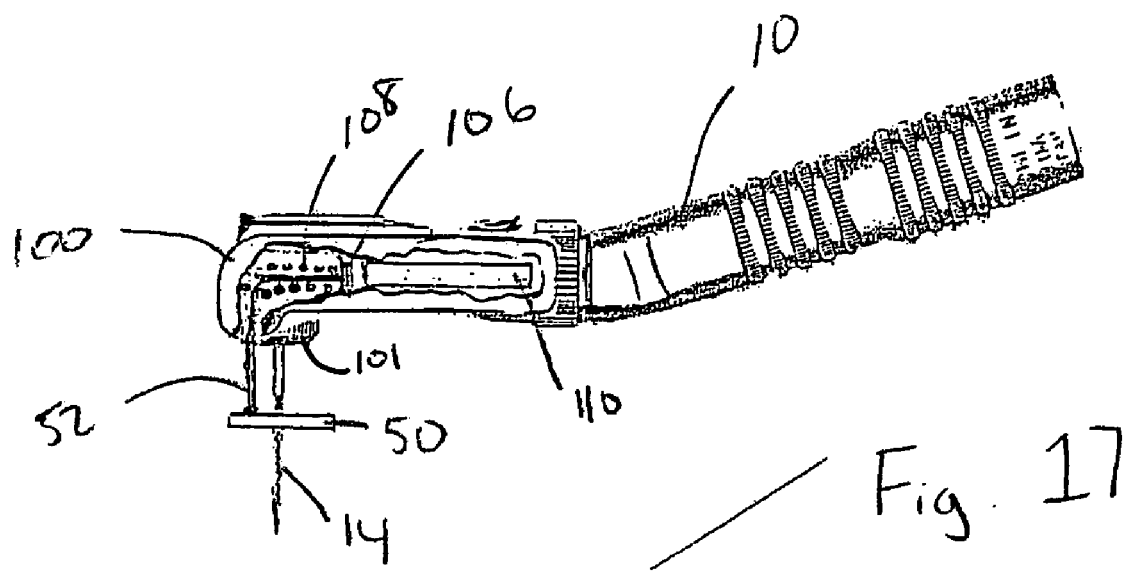
FIG. 17, is a side view of the dial stem housing from FIG. 13, attached to a drill hand set, in accordance with one embodiment of the present invention.
Figure 18:
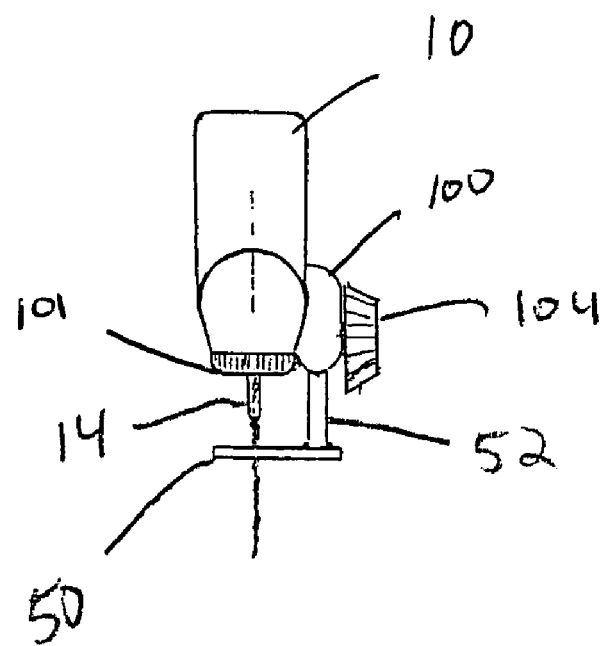
FIG. 18, is a front view of the dial stem housing from FIG. 13, attached to a drill hand set, in accordance with one embodiment of the present invention.

Also disposed with dial stem housing 100 is a tooth bar 110, configured to abut against the end of stem 52. Additionally, as illustrated in FIGS. 14 and 15, height dial 104 extends within dial stem housing 100 and terminates in a toothed wheel portion 112, supported on a wheel support 114. Close up views of tooth bar tooth bar 110 and toothed wheel portion 112 are illustrated in FIG. 16. A top view of toothed wheel portion 112, coupled to height dial 104, is illustrated in FIG. 15. Additionally, FIGS. 17 and 18 illustrate various views of dial stem housing 100 disposed on drill hand set 10 in accordance with one embodiment of the present invention.

Thus, as illustrated in FIGS. 13 and 14, the height of bottom of jig ring 50 can be adjusted by the dentist by simply turning height dial 104 to the desired height as indicated. By turning dial 104 to a higher height setting, the inner toothed wheel portion 112 acts in gear fashion against the teeth of tooth bar 110, which in turn forces abutting stem 52 in a first direction out of dial stem housing 100. If the dentist requires a lower height setting, they can simply allow biasing spring 108 to act against spring flange 106, moving stem 52 down to the lower height settings.

It is important to note that for locking purposes a simple clutch mechanism can be added to height dial 104 and attached toothed wheel portion 112, so that toothed bar 110, engaged with toothed wheel portion 112 remains locked until the clutch is engaged. Any typical clutch mechanism can be employed such as a push clutch, where height dial 104 remains locked until a slight inward pressure, towards dial stem housing 100, is applied. It is under stood that any similar clutch system, used for securing tooth bar 112 in place during drilling, is also within the contemplation of the present invention.

Using the same measurements equations as discussed in detail in the first and second embodiments, the necessary total height is calculated using a simple formula.

$$HS-HR=DiS$$

where HS=Height of Shank; HR=Height of Root; and DiS=Dial Setting

For example, if the dentist is using a 27 mm drill shank 14, and the height or depth of the root is 16 mm, then height dial 104 is moved to the appropriate 11 mm setting. This action moves toothed bar 110 against stem 52, such that stem 52 is moved outward from dial stem housing 100, until the distance between the bottom of drill hand set 10 and the bottom of jig ring 50 is set to 11 mm, allowing only 16 mm of drill shank 14 to extend below the bottom a jig ring 50. As such, when drill shank 14 is drilled into the root of the affected tooth, drill hand set 10 will be stopped when the bottom of jig ring 50 contacts the top of the tooth, allowing for exactly 16 mm of drilling into the affected tooth root. It is understood that such a dial stem housing can be manufactured in accordance with any desired height requirements.

In another embodiment of the present invention, a screw stem housing 200 is provided, which roughly mirrors the shape of the drilling end of drill hand set 10, as illustrated in FIG. 17. Screw stem housing 200 is preferably constructed of the same material as drill handset 10, however, it can be constructed of any surgical grade metal or polymer that is able to support the attached stem 52. Screw stem housing 200 is configured to be attached to drill hand set 10 at the drilling end, such that the end 201 of housing 200, where stem 52 emerges, is roughly co-equal in height with the point where drill shank 14 emerges from drill hand set 10.

Screw stem housing 200 is fitted with a screw opening 202 along the side that is exposed when it is attached to drill hand set 10. Dial opening 202 is configured to support a height screw 204. Screw stem housing 200 further maintains a height window 206 such that height measurements, indicated or marked onto stem 52, may be viewed through the outer wall of screw stem housing 200.

Figure 23:
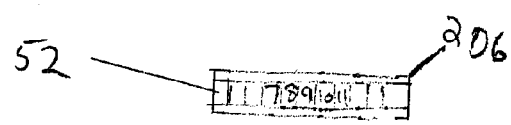
FIG. 23 is a side view of the stem window from FIG. 19, in accordance with one embodiment of the present invention.

As illustrated in close up FIG. 23, within screw stem housing 200, stem 52 is labeled consecutively with height measurement ranging in either 0.5 mm or 1 mm steps. Typically, the height measurements range from 7 mm up to 12 mm, however, it is understood that the both the range, increments and denomination of the measurements on stem 52 can be manufactured in a variety of heights in accordance with any desired specifications.

Regardless of the numbering systems used to label stem 52, each height marking on stem 52 represents a different height that stem 52 will extend from the bottom of drill hand set 10, (bottom being defined by the point at which drill shank 14 emerges from drill hand set 10) until it reaches the bottom of the attached jig ring 50.

Figure 20:
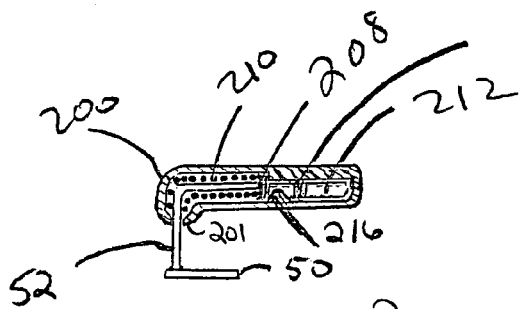
FIG. 20 is a cross-sectional side view of a jig ring, stem and screw stem housing from FIG. 19, in accordance with one embodiment of the present invention.

FIG. 20 illustrate the mechanism disposed in housing 200. As illustrated in FIG. 20, stem 52 is outfitted with a spring flange 208 disposed on stem 52, within screw stem housing 200. On the jig ring 50 side of flange 208, a biasing spring 210 is positioned within screw stem housing 200 in such a way so as to act against flange 208 to bias stem 52 in a direction away from the drilling end of drill hand set 10 and towards the rear of screw stem housing 200.

Figure 21:
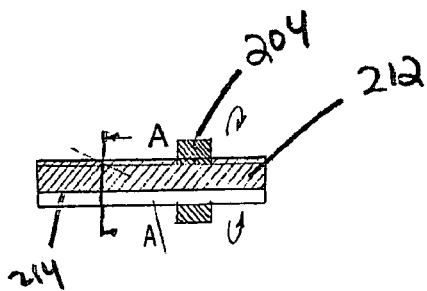
FIG. 21 is a side view of a sliding screw bar and height screw, in accordance with one embodiment of the present invention.
Figure 22:
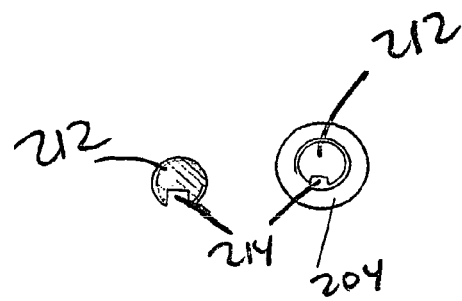
FIG. 22, is a cross section of the sliding screw bar and height screw from FIG. 21, in accordance with one embodiment of the present invention.
Figure 24:
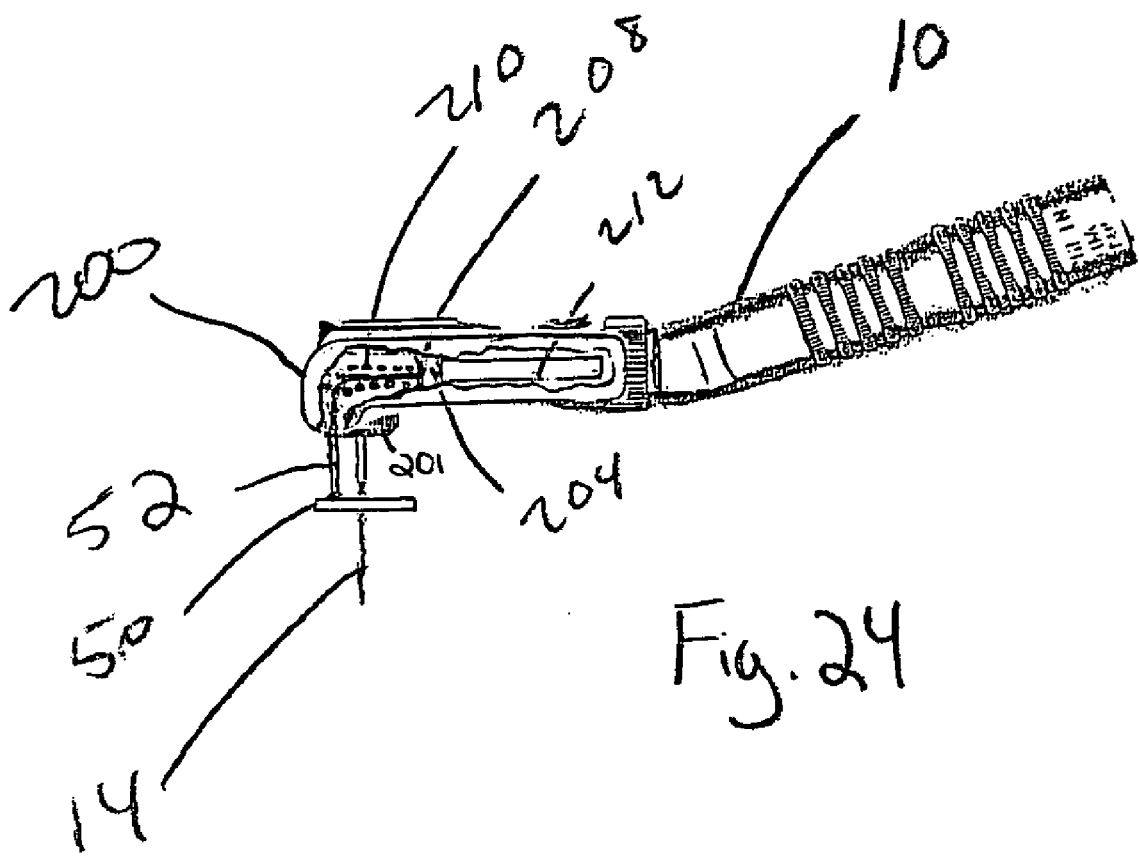
FIG. 24, is a side view of the screw stem housing from FIG. 19, attached to a drill hand set, in accordance with one embodiment of the present invention.
Figure 25:
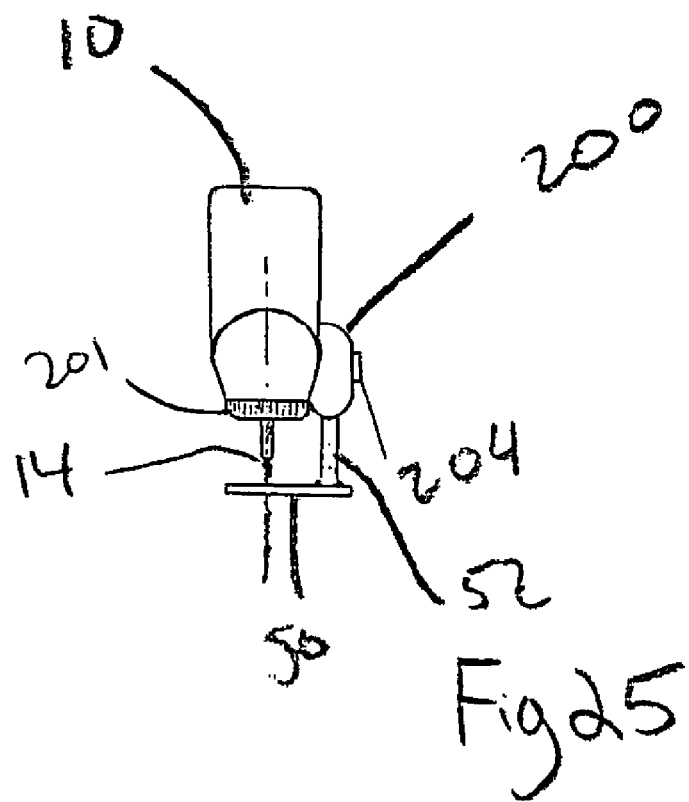
FIG. 25, is a front view of the screw stem housing from FIG. 19, attached to a drill hand set, in accordance with one embodiment of the present invention.

Also disposed with screw stem housing 200 is a threaded screw bar 212, configured to abut against the end of stem 52. As illustrated in FIGS. 21 and 22, threaded screw bar 212 is fashioned with a slide groove 214 and an external threading. A screw bar support 216 is disposed on the bottom of screw stem housing 200, configured to engage slide groove 214. FIGS. 24 and 25 illustrate various views of screw stem housing 200 disposed on drill hand set 10 in accordance with one embodiment of the present invention.

Figure 19:
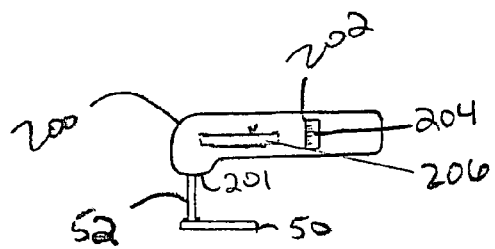
FIG. 19 is a side view of a jig ring, stem and screw stem housing, in accordance with another embodiment of the present invention.

Thus, as illustrated in FIGS. 19 and 20, the height of bottom of jig ring 50 can be adjusted by the dentist by turning height screw 204 within screw opening 202 to the desired height as indicated on the moving stem 52, viewed through height window 206. By turning height screw 204, a screw action is performed on threaded screw bar 212, which in turn slides along screw bar support 216 on groove 214, which in turn forces abutting stem 52 out of screw stem housing 200 in a first higher height direction. If the dentist requires a lower height setting, they can slowly reverse height screw 204 and allow biasing spring 210 to act against spring flange 208, moving stem 52 down to a lower height setting. The final height level is indicated by consulting the height marked stem 52 through height window 206.

Using the same measurements equations as discussed in detail in the first and second embodiments, the necessary total height is calculated using a simple formula.

$$HS-HR=HSS$$

where HS=Height of Shank; HR=Height of Root; and HSS=Height Screw Setting

For example, if the dentist is using a 25 mm drill shank 14, and the height or depth of the root is 17 mm, then height screw 204 is turned to the appropriate 8 mm setting. This action moves threaded screw bar 212 against stem 52, such that stem 52 is moved outward from screw stem housing 200, until the distance between the bottom of drill hand set 10 and the bottom of jig ring 50 is set to 8 mm, allowing only 17 mm of drill shank 14 to extend below the bottom a jig ring 50. As such, when drill shank 14 is drilled into the root of the affected tooth, drill hand set 10 will be stopped when the bottom of jig ring 50 contacts the top of the tooth, allowing for exactly 17 mm of drilling into the root of the affected tooth. It is understood that such a screw stem housing 200 can be manufactured in accordance with the desired requirements.

It is further contemplated that many other advances can be easily applied to the present system. For example, using the same stem 52 and jig ring 50 an external housing could be developed using essentially the same method of preventing a dentist from over or under drilling a root canal. Using a simple ring to support stem 52 on the outside of the drilling end of drill hand set 10 and a locking cam, a graduated stem 52 can be used to the same ends.

Likewise, it is further contemplated that a digitizing mechanism could be added to the stem housing described above, particularly screw stem housing 200 and dial stem housing 100, making it is easier to read the height setting on the device. A digital component may even be added to an actuating device so that the height can actually be set digitally as well as read digitally.

While only certain features of the invention have been illustrated and described herein, many modifications, substitutions, changes or equivalents will now occur to those skilled in the art. It is therefore, to be understood that this application is intended to cover all such modifications and changes that fall within the true spirit of the invention.

What is claimed is:

1. A device for use in an endodontic root canal, performed using a dental drill hand set, said device comprising:
   a first upper unit coupled to said drill hand set, said first upper unit being cylindrical in shape and having a first drill shank shaft therethrough and wherein said first upper unit has a first threading on its outside surface; and
   a second bottom unit being cylindrical in shape and having a second drill shank shaft therethrough, said second bottom unit has a second corresponding threading on its inside surface, wherein when said second bottom unit is screwed onto said first upper unit a root canal jig is formed having a set height, said root canal jig having a series of adjustment markers, positioned on said first upper unit of said root canal jig, said adjustment markers configured to denote the combined height of said root canal jig from the bottom of said second bottom unit to the top of said first upper unit, allowing a shank from said drill hand set to pass through said first and second drill shank shafts, such that when said drill shank of said drill hand set is drilled into an affected tooth for a root canal, said drill shank is prevented from drilling along its entire length into the root of said affected toot when the bottom of said root canal jig contacts the top of the tooths, wherein said root canal jig is set to a particular height such that the combined height of said root canal jig added to the total depth of the root of the affected tooth is equal to the total length of the drill shank that extends beyond the bottom of said drill hand set such that when a dentist is drilling said root of said affected tooth, the amount of said drill shank that extends below the bottom of said root canal jig is equal to the depth of said root being drilled.

2. The device as claimed in claim 1, further comprising a locking ring, having a third corresponding threading located on its inside surface, configured to screw down along said first upper unit of said root canal jig down onto a top of said second bottom unit of said root canal jig, so as to prevent any relative movement between said upper first unit and said lower bottom unit of said root canal jig.

3. The device as claimed in claim 1, further comprising a primary maker, positioned on said second bottom unit of said root canal jig, said primary marker configured to display the height of said second bottom unit.

4. A device for use in an endodontic root canal, performed using a dental drill hand set, said device comprising:
   a jig ring having a drill shank opening, configured to rest on the top of the affected tooth to be drilled;
   a stem, coupled to said jig ring; and
   a housing, coupled to said drill hand set, said housing configured to secure said stem therein, such that the bottom of said jig ring, coupled to said stem, can be secured from the bottom of said housing, proximate to the drilling end of said drill hand set at a series of varying heights, said housing having a notch opening having a plurality of dimple acceptors therein, each of said dimple acceptors having a corresponding measurement associated therewith.

5. The device as claimed in claim 4, wherein said jig ring is a horseshoe ring.

6. The device as claimed in claim 4, wherein said stem is constructed of a sturdy, flexible nickel-titanium alloy.

7. The device as claimed in claim 4, wherein said stern further comprises a spring flange, and wherein said housing further comprises a biasing spring, wherein said biasing spring acts on said spring flange of said stem, forcing said stem into said housing, in direction away from the drilling end of said drill hand set.

8. The device as claimed in claim 7, wherein said stem further comprises a dimple, said dimple being configured to fit within one of said dimple acceptors, having a corresponding measurement equal to a desired height measurement, said desired height measurement being equal to the distance between the bottom of said jig ring and the edge of the drilling end of said drill hand set.

9. The device as claimed in claim 4, wherein said housing further comprises a height dial having a plurality of incremented height measurements marked thereon.

10. The device as claimed in claim 9, wherein said stem further comprises a spring flange, and wherein said housing further comprises a biasing spring, wherein said biasing spring acts on said spring flange of said stem, forcing said stem into said housing, in direction away from the drilling end of said drill hand set.

11. The device as claimed in claim 10, wherein said housing further comprises a toothed bar, positioned within said housing on the side of said spring flange opposite said biasing spring, and wherein said height dial further comprises a toothed wheel engaged with said tooth bar.

12. The device as claimed in claim 11, wherein a desired height measurement is selected, said height dial is rotated to the correct incremental measurement thereon, thus turning said attached toothed wheel and moving said engaged toothed bar, forcing said stem out of said housing to said desired height measurement, said desired height measurement being equal to the distance between the bottom of said jig ring and the edge of the drilling end of said drill hand set.

13. The device as claimed in claim 4, wherein said housing further comprises a height screw associated with a plurality of incremented height measurements marked on said stem and viewable through a height window in said housing.

14. The device as claimed in claim 13, wherein said stem further comprises a spring flange, and wherein said housing further comprises a biasing spring, wherein said biasing spring acts on said spring flange of said stem, forcing said stem into said housing, in direction away from the drilling end of said drill hand set.

15. The device as claimed in claim 14, wherein said housing further comprises a threaded screw bar, positioned within said housing on the side of said spring flange opposite said biasing spring, and wherein the threading within said height screw is engaged with said threaded screw bar.

16. The device as claimed in claim 15, wherein a desired height measurement is selected, said height screw is rotated until the desired height measurement is indicated in said height window, thus moving said threaded screw bar, forcing said stem out of said housing to said desired height measurement, said desired height measurement being equal to the distance between the bottom of said jig ring and the edge of the drilling end of said drill hand set.

17. A device far use in an endodontic root canal, performed using a dental drill hand set, said device comprising:

a root canal jig having a top and bottom and an adjustable height, said top of said root canal jig being attachable to said dental drill hand set, said root canal jig having a series of adjustment markers, positioned on said ton of said root canal jig, said adjustment markers configured to denote the combined height of said root canal jig, said root canal jig configured to allow a drill shank to pass therethrough, wherein said root canal jig is configured to allow a portion of said drill shank, less tan the total height of said drill shank, to be exposed out from said bottom of said root canal jig, such that when said bottom of said root canal jig contacts the top of an affected tooth, said drill shank is prevented from drilling any farther into said affected tooth, wherein said root canal jig is set to a particular height such that the combined height of said root canal jig added to the total depth of the root of the affected tooth is equal to the total length of the drill shank that extends beyond the bottom of said drill hand set such that when a dentist is drilling said root of said affected tooth, the amount of said drill shank that extends below the bottom of said root canal jig is equal to the depth of said root being drilled.

* * * * *